United States Patent
Fouache et al.

(10) Patent No.: US 6,500,649 B2
(45) Date of Patent: Dec. 31, 2002

(54) PROCESS FOR THE CONVERSION OF ORGANIC MATERIALS, PARTICULARLY SACCHARIDE MATERIALS, COMPRISING AN ENZYMATIC OXIDATION STEP IN THE PRESENCE OF RUTHENIUM OR PALLADIUM

(75) Inventors: Catherine Fouache, Sailly La Bourse (FR); Rodolphe Tamion, Allouagne (FR); Guy Fleche, Hazebrouck (FR); Didier Moine, Merville (FR); Patrick Fuertes, Lambersart (FR)

(73) Assignee: Roquette Freres, Lestrem (FR)

( * ) Notice: Subject to any disclaimer, the term of this patent is extended or adjusted under 35 U.S.C. 154(b) by 0 days.

(21) Appl. No.: 09/728,437

(22) Filed: Dec. 1, 2000

(65) Prior Publication Data

US 2001/0003651 A1 Jun. 14, 2001

(30) Foreign Application Priority Data

Dec. 7, 1999 (FR) .............................. 99 15434

(51) Int. Cl.⁷ .............................. C12P 19/00
(52) U.S. Cl. .................. 435/72; 435/105; 435/100; 435/137; 435/158
(58) Field of Search .................. 435/72, 105, 100, 435/137, 158

(56) References Cited

U.S. PATENT DOCUMENTS

| 4,246,347 A | 1/1981 | Neidleman et al. |
| 4,321,324 A | 3/1982 | Maselli et al. |
| 4,351,902 A | 9/1982 | Neidleman et al. |
| 4,423,149 A | 12/1983 | Amon, Jr. et al. |
| 4,460,686 A | 7/1984 | Hartmeier |
| 4,568,645 A | 2/1986 | Koths et al. |
| 4,569,910 A | 2/1986 | Koths et al. |
| 4,569,913 A | 2/1986 | Koths et al. |
| 4,569,915 A | 2/1986 | Ring |
| 4,650,758 A | 3/1987 | Shaked et al. |
| 5,262,314 A | 11/1993 | Anton et al. |
| 5,897,995 A | 4/1999 | Vroemen et al. |

FOREIGN PATENT DOCUMENTS

| WO | WO 81/03664 | 12/1981 |
| WO | WO 81/03666 | 12/1981 |
| WO | WO 97/24454 | 7/1997 |

OTHER PUBLICATIONS

Carter, Robert S. et al., "Stability studies on the immobilized glucose oxidase/catalase enzyme system",Enzyme Eng., 1980, vol. 5, pp. 321–324, XP000861930.

Nakao K et al. "Production of gluconic acid with immobilized glucose oxidase in airlift reactors", Chemical Engeneering Science, 1997, vol. 52, n°21–22, pp. 4127–4133.

Enzyme nomenclature, 1992, pp. 55–60.

Huwig A. et al., "Laboratory procedures for producing 2–keto–D–glucose . . . " Journal of Biotechnology 32, 1994, pp. 309–315.

Haltrich D. et al., "A convinient Enzymatic Procedure for the production of Aldose–Free D–tagatose", Enzyme Engeneering, Dec. 13 1998, (864), pp. 295–299,.

Leitner C. et al., "The cetus process revisited: a novel enzymatic . . . ", Biocatalysis and Transformation, vol. 00, pp. 1–18 (1998).

Duvnjak Z., "The Immobilization of Glucose Oxidase to Manganese Oxide", Biotechnology and Bioengeneering, 1976, vol. XVIII, pp. 737–739.

Cho Y. K., "The influence of Peroxide–stabilizing Agents on Enzyme Deactivation by $H_2O_2$", Biotechnology and Bioengeneering, 1977, vol. XIX, pp. 157–158,.

Cho Y. K., "Enzyme Immobiliztion on Activated Carbon : Alleviation of Enzyme Deactivation by Hydrogen Peroxide", Biotechnology and Bioengeneering, 1977, vol. XIX, pp. 769–775,.

Primary Examiner—Francisco Prats
(74) Attorney, Agent, or Firm—Henderson & Sturm LLP

(57) ABSTRACT

A process for the conversion of an organic material comprising an oxidation step during which an organic material undergoes the oxidising action of an enzymatic means capable of generating hydrogen peroxide, wherein said oxidation step is carried out, wholly or partly, in the presence of 0.001% to 1% of a metal selected from ruthenium, palladium and mixtures thereof.

9 Claims, No Drawings

PROCESS FOR THE CONVERSION OF ORGANIC MATERIALS, PARTICULARLY SACCHARIDE MATERIALS, COMPRISING AN ENZYMATIC OXIDATION STEP IN THE PRESENCE OF RUTHENIUM OR PALLADIUM

FIELD OF THE INVENTION

The present invention relates to a new process for the conversion of organic materials, particularly saccharide materials, comprising an oxidation step carried out under particular conditions, namely combining, at least at a given moment, a means of enzymatic oxidation capable of generating hydrogen peroxide and at least one particular metal, namely ruthenium and/or palladium.

The invention also relates to a process as described above comprising an additional step involving the oxidation or reduction of the material oxidised enzymatically beforehand.

In particular, the claimed process makes it possible to obtain, in a simple, rapid and inexpensive manner, organic materials, particularly those of a saccharide nature, oxidised with high selectivity then optionally reduced or re-oxidised, having numerous industrial applications, including the use as synthesis intermediates, such as glucosone, galactosone, gluconic, 2-keto-gluconic or isoascorbic acids, fructose, sorbitol, mannitol etc.

The term "organic materials" within the meaning of the present invention means both saccharide materials and non-saccharide organic materials.

The latter include alcohols and organic acids of a non-saccharide nature such as, for example, lower alcohols including methanol, fatty alcohols, glycerol, cholesterol, polyvinyl alcohols, hydroxycarboxylic acids including malic acid, the respective derivatives thereof and, generally, all organic products other than saccharides which are potentially capable of being oxidised enzymatically with the concomitant production of hydrogen peroxide.

As mentioned, the process forming the subject matter of the invention may be applied advantageously to saccharide materials, this idea being in no way limiting and including linear, cyclic or branched monosaccharides, disaccharides, trisaccharides, oligosaccharides and mixtures of these products such as hydrolysates of starch, insulin or cellulose.

It may also be applied to saccharide materials which have undergone, before the characteristic step of enzymatic oxidation, at least one step involving chemical, enzymatic and/or physical modification, particularly hydrolysis, oxidation or hydrogenation and/or at least one purification step.

Preferably, the saccharide material is chosen from the group comprising monosaccharides, disaccharides, oxidised or hydrogenated derivatives of monosaccharides and disaccharides, and any mixtures of at least any two of these products, independently of the process by which such products were obtained.

Monosaccharides may consist, in particular, of pentoses or hexoses such as xylose, arabinose, ribose, glucose, galactose, mannose, sorbose or fructose.

Disaccharides may consist, in particular, of maltose, isomaltose, lactose, lactulose, cellobiose or sucrose.

As mentioned, the process according to the invention may also be applied to organic materials composed of purified or unpurified monosaccharides or disaccharides which have already been modified, particularly which have already been oxidised or hydrogenated.

The oxidised monosaccharides and disaccharides undergoing the characteristic step of enzymatic oxidation according to the invention may, in particular, correspond to the products of the oxidation, in one or more places, of the monosaccharides and disaccharides listed above and, in particular, may consist of any of gluconic, glucaric, 5-ketogluconic, galactonic, galactaric, gulonic, maltobionic or lactobionic acids, said acids being in the free and/or lactonised and/or salt form.

The lactonised form may, by way of example, consist of a gluconolactone, a galactolactone or a gulonolactone.

The hydrogenated monosaccharides and disaccharides may, in particular, correspond to the products of relatively thorough catalytic hydrogenation of the above-mentioned monosaccharides and disaccharides.

It is widely known that monosaccharides or disaccharides, optionally oxidised or hydrogenated already, may be oxidised enzymatically, particularly by oxidoreductases capable of using oxygen as a hydrogen acceptor and hence capable of generating hydrogen peroxide ($H_2O_2$) in the reaction medium.

These are, in particular, enzymes of Group 1.1.3 as defined in the document "ENZYME NOMENCLATURE", revised periodically by the International Union of Biochemistry and Molecular Biology. The nomenclature of such enzymes is recapitulated on pages 55 to 60 of the 1992 edition of said document.

These are, inter alia, enzymes having at least one of the glucose oxidase, hexose oxidase, galactose oxidase or pyranose oxidase activities.

BACKGROUND OF THE INVENTION

Thus, reference has been made regularly, particularly for about twenty years, to the use of pyranose oxidase (also known, inter alia, as "glucose 2-oxidase", "pyranose: oxygen 2-oxidoreductase" or more simply "P2O") for the enzymatic conversion of monosaccharides, optionally already oxidised, to their equivalents oxidised in the 2 position, and in particular for the conversion of glucose to glucosone or galactose to galactosone. These products are synthesis intermediates of great interest for obtaining products such as fructose, sorbitol, mannitol or tagatose which, on their own or in mixture, have wide fields of application, particularly in the food, pharmaceutical and chemical industries.

For several decades, there has also been wide recourse to the use of glucose oxidase (also known, inter alia, as "glucose oxyhydrase", "beta-D-glucose: oxygen 1-oxidoreductase" or more simply "GOD") for the preparation of gluconic acid, in the free, lactonised and/or salt form, from glucose.

However, one of the major disadvantages of the above-mentioned enzymes is that hydrogen peroxide is generated concomitantly and in equimolar quantities with the desired oxidised product. However, it is acknowledged that the presence of hydrogen peroxide is, on the whole, disadvantageous for the activity of an oxidoreductase such as pyranose or glucose oxidase, and efforts are generally made to remove hydrogen peroxide wholly or partly from the reaction medium during the course of the enzymatic oxidation reaction.

Various means of an enzymatic, chemical or physical nature have been proposed for removing or decreasing hydrogen peroxide or at least the adverse effects associated with the generation and presence of this compound in the complex medium which the enzymatic oxidation medium constitutes.

The means most often described consists in the use of catalase in the free or immobilised form, with a view to decomposing hydrogen peroxide enzymatically. This use is described in numerous patents such as the patents WO 81/03664 and WO 81/03666 published in 1981 in the name of STANDARD BRANDS, the subsequent patents U.S. Pat. Nos. 4,351,902, 4,423,149, 4,568,645, 4,569,910, 4,569,913, 4,569,915 and 4,650,758 in the name of CETUS CORPORATION, WO 97/24454 in the name of GENENCOR INTERNATIONAL INC and U.S. Pat. No. 5,897,995 in the name of GIST-BROCADES B.V.

The use of catalase in combination with a glucose oxidase has also been mentioned, where necessary also illustrated by examples, in the articles or patents below:

"STABILITY STUDIES ON THE IMMOBILIZED GLUCOSE OXIDASE/CATALASE ENZYME SYSTEM", R. S. CARTER et al, ENZYME ENG., (1980), 5, 321–324,

U.S. Pat. No. 4,460,686, published in 1984 in the name of BOEHRINGER INGELHEIM,

"Production of gluconic acid with immobilized glucose oxidase in airlift reactors", K. NAKAO et al, CHEMICAL ENGINEERING SCIENCE, (NOV. 1997), VOL. 52, no. 21–22, 4127–4133.

The use of catalase in combination with another oxidoreductase, namely a glycolate oxidase (EC 1.1.3.15), has also been illustrated by examples in U.S. Pat. No. 5,262,314 published in 1993 in the name of E.I. Du Pont de Nemours and Co.

The use of catalase has also been described, inter alia, in the following recent scientific articles:

"Laboratory procedures for producing 2-keto-D-glucose, 2-keto-D-xylose and 5-keto-D-fructose from D-glucose, D-xylose and L-sorbose with immobilized pyranose oxidase of *Peniophoro gigantea*", A. HUWIG et al, Journal of Biotechnology 32, 309–315 (1994), "A Convenient Enzymatic Procedure for the Production of Aldose-Free-D-Tagatose", D. HALTRICH et al, ANNALS NEW YORK ACADEMY OF SCIENCES, 864, 295–299 (1998), "The CETUS Process revisited: a novel enzymatic alternative for the production of aldose-free D-fructose", C. LEITNER et al, Biocatalysis and Biotransformation, Vol., 00, 1–18 (1998).

Other routes already advocated for the removal/decrease of hydrogen peroxide or of its adverse effects in a reaction medium as envisaged here consist in the use of chemical means such as:

Manganese oxides said to be capable of decomposing $H_2O_2$ according to the article "The Immobilization of Glucose Oxidase to Manganese Oxide", Z. DUVNJAK et al, BIOTECHNOLOGY AND BIOENGINEERING, VOL. XVIII, 737–739 (1976), but which are said not to be sufficiently effective according to U.S. Pat. No. 4,460,686 mentioned above and would not, in fact, be able to act as a substitute for catalase, as follows from the examples of U.S. Pat. No. 5,262,314, Quinine sulfate or urea which are said to be capable of stabilising glucose oxidase in the presence of $H_2O_2$ according to the article "The Influence of Peroxide—Stabilizing Agents on Enzyme Deactivation by $H_2O_2$", Y. K. CHO et al, BIOTECHNOLOGY AND BIOENGINEERING, VOL. XIX, 157–158 (1977), Activated carbon which is said to be capable of inactivating $H_2O_2$ according to the article "Enzyme Immobilization on Activated Carbon: Alleviation of Enzyme Deactivation by Hydrogen Peroxide", Y. K. CHO et al, BIOTECHNOLOGY AND BIOENGINEERING, VOL. XIX, 769–775 (1977) and according to the above-mentioned article by R. S. CARTER, Alkenes which are said to be capable of "consuming" $H_2O_2$ and thus forming recoverable glycols or alkoylene oxides according to U.S. Pat. No. 4,321,324 in the name of CETUS CORPORATION, Platinum which, in the presence of P2O-producing mycelium and a dilute solution of glucose (2.5%), is said to be capable of decomposing $H_2O_2$ according to the patent WO 81/03666 mentioned above, and the use of which, as a substitute for catalase for stabilising glycolate oxidase, is advocated in U.S. Pat. No. 5,262,314 mentioned above, Stabilisation of pyranose oxidase by amidination according to the above-mentioned U.S. Pat. No. 4,650,758, Purification of pyranose oxidase by removing the parasitic "pyranosone dehydratase" activity according to the above-mentioned U.S. Pat. No. 4,569,913.

Other documents advocate the removal (of the adverse effects) of hydrogen peroxide by combining a physical means (semi-permeable membrane) with an enzymatic means (catalase) or chemical means (alkene) as described in the above-mentioned patents WO 81/03664 and U.S. Pat. No. 4,321,324.

Metals other than platinum have been advocated with a view to stabilising the activity of glucose oxidase ("GOD") by decomposition of hydrogen peroxide ($H_2O_2$).

This is the case, inter alia, with ruthenium, the use of which is envisaged in the above-mentioned article by R. S. CARTER. This document does not, however, specify the exact conditions of use of this metal in the oxidation reaction medium, and particularly the ruthenium content of said medium, and the ratio of glucose oxidase/catalase activity when the latter is present. On the other hand, this document underlines the gradual "poisoning" of the ruthenium by the gluconic acid generated and draws conclusions about the insufficient protective effect of this metal towards GOD from the point of view of long-term industrial trials.

This insufficient ability of ruthenium to improve the stability of GOD, including immobilised GOD in the presence of catalase, is underlined in column 2, lines 46–51 of the U.S. Pat. No. 4,460,686 mentioned above.

This lack of effectiveness of ruthenium as a substitute for catalase for stabilising an oxidoreductase such as glycolate oxidase follows clearly, moreover, from the U.S. Pat. No. 5,262,314 published subsequently in 1993.

Examples 3, 5 and 13 of said patent show that this metal, even if used in a very large quantity, i.e. greater than 2.5% expressed as dry weight with respect to the dry substance of the reaction medium, or greater than 5% expressed as dry weight with respect to the dry weight of the substrate to be oxidised, does not make it possible to obtain:

high yields of oxidised substrate, these yields always being less than 35%, a high residual "oxidoreductase" activity, this activity also always being less than 35%.

This is the case, in particular, when ruthenium is used on an activated carbon support according to example 5 of said patent.

The use of 0.615 g of a catalyst based on 5% ruthenium on activated carbon, that is, about 5.4% ruthenium (dry/dry) with respect to the glycolic acid used, or about 2.7% ruthenium (dry/dry) expressed with respect to the dry substance of the reaction medium, allows at best the following to be obtained after 22 hours' reaction:

a glyoxylate yield of 32.5%, and a residual "glycolate oxidase" activity of 17%.

Consequently, U.S. Pat. No. 5,262,314 advocates the use of extremely large quantities of "non-enzymatic catalysts" of a very varied nature such as manganese or copper oxides, ruthenium, platinum, palladium, lead, soluble salts or chelates of manganese, copper, nickel, cobalt, zinc, iron or chromium, activated carbon or certain imidazole derivatives, from the point of view of replacing the use of catalase.

More recently, consideration has been given, within the context of reactions carried out in particular pieces of equipment (airlift reactors), to substituting catalase by fine particles of palladium contained in a quantity of 4 wt. % in alginate beads having a density of around 1 g/cm$^3$ and in which GOD is also immobilised.

The exact quantities of palladium used effectively in the reaction medium, particularly in terms of the total dry substance of said medium (including alginate beads) and/or the dry weight of the substrate alone to be oxidised (glucose) are not specified. However, it is pointed out in the last paragraph of the chapter "Optimal operating conditions" on page 4132 of said document that:

the optimum initial concentration of the glucose solution is 10 g/l, and the optimum volume ratio of the alginate beads with respect to the total volume of beads+glucose solution or "gel bead content" is 0.4.

Consequently, also in view of the presumed density of said glucose solution ($\approx$1 g/cm$^3$) and the very low usual dry substance content of alginate beads intended to contain an enzyme (dry substance<20%, generally<10%), it is deduced by calculation that the authors advocate a quantity of palladium whatever the circumstances;

greater than 250%, expressed as dry/dry with respect to the quantity of substrate (glucose), and greater than 15%, expressed as dry weight with respect to the total dry substance of the reaction medium (including beads).

The overall result of the above is that, in the case of glucose oxidase and glycolate oxidase, metals such as, inter alia, ruthenium or palladium cannot be effective substitutes for catalase unless, optionally, they are used in necessarily very high and hence extremely expensive quantities.

Moreover, in the case of pyranose oxidase, there is no option but to ascertain that the most recent prior art, represented by the examples of the above-mentioned CETUS CORPORATION patents and scientific articles, envisages in practice only catalase as the principal means of removing hydrogen peroxide and its adverse effects.

In particular, catalase may be physically combined with the oxidoreductase (pyranose oxidase, glucose oxidase in particular) by way of enzymatic complexes naturally present in various microorganisms or pre-mixtures of enzymes of different origins, but also by means of co-immobilisation on the same support, these variants being described, for example, in the U.S. Pat. Nos. 4,569,910, 4,650,758, 4,351, 902 and 5,897,995 mentioned above.

Catalase may also be combined with bovine serum albumin ("BSA" acting as a stabiliser or protector of the oxidoreductase as described in the articles by HALTRICH and LEITNER mentioned above. The precise mode of action of BSA is poorly understood but, according to LEITNER this protein could, in particular, protect pyranose oxidase and also catalase from the adverse effects of glucosone. Other protective agents may consist of casein, methionine, quinine or mannitol, sorbitol or glycerol according to the U.S. Pat. No. 5,897,995.

Whatever the case, it is known that catalase is also inactivated by hydrogen peroxide and that it is necessary, in practice, to use it in large quantities, in any case in a large excess with respect to the quantities of oxidoreductases used in conjunction therewith.

The patents WO 97/24454 and U.S. Pat. No. 5,897,995 published very recently envisage ratios between the number of units of catalase and the number of units of oxidoreductase (glucose oxidase) used in the reaction medium (hereinafter known as the C/O ratios) of the order of 40–80 (WO 97/24454) or even equal to 140 (U.S. Pat. No. 5,897, 995).

Finally, the articles by HALTRICH and LEITNER mentioned above advocate a CIO ratio of 1000, combined with the use of BSA in a quantity of 5 mg/ml of reaction medium, with the possibility of recycling the oxidoreductase (pyranose oxidase) and BSA—unlike the catalase used which is unstable—after their extraction from the reaction medium by ultrafiltration.

Another teaching by LEITNER relates to the fact that the platinum deposited on activated carbon cannot, in fact, be used as a substitute for catalase because its use results in a loss of more than 95% of the P2O activity under standard operating conditions.

Consequently, in spite of the cost of using catalase, no serious consideration was given, until then, to questioning the growing interest and use.

SUMMARY OF THE INVENTION

After considerable research, a new means has now been developed for the effective preparation of organic materials oxidised enzymatically such as, for example, glucosone or gluconic acid, said means making it possible, if desired, to obtain said materials in the presence of reduced or even zero quantities of catalase, and/or protective agent such as BSA.

The Applicant company has, in particular, found that, surprisingly and unexpectedly, ruthenium and palladium in small quantities could, unlike platinum in particular, be used advantageously as a substitute for catalase and allow an oxidoreductase such as pyranose or glucose oxidase to act rapidly with a high yield and excellent selectivity.

DETAILED DESCRIPTION OF THE INVENTION

More specifically, the present invention relates to a process for the conversion of an organic material comprising an oxidation step during which an organic material undergoes the oxidising action of an enzymatic means capable of generating hydrogen peroxide, this process being characterised in that said oxidation step is carried out wholly or partly in the presence of 0.001% to 1% of a metal selected from ruthenium, palladium and mixtures thereof, these percentages being expressed as total dry weight of ruthenium and palladium with respect to the total dry weight of the reaction medium.

Advantageously, said metal is present in an amount in the range 0.005% to 0.2%

As mentioned, it is not obligatory that said metal be present in the reaction medium perfectly simultaneously with the means of enzymatic oxidation; one may be introduced into the reaction medium and/or withdrawn from the reaction medium before the other. Ruthenium and/or palladium may be introduced in any suitable forms, particularly in the immobilised form on a support, obtained by any known method, particularly impregnation or ion exchange. The support may be composed, for example, of activated carbon, peat, zeolite, titanium dioxide or a synthetic polymer of the carbon fibre type. An undeniable advantage of the process claimed here is that it allows the recycling of said metal, which is generally impossible with an ordinary catalase.

The organic materials, particularly of a saccharide nature, that may be used as a substrate for at least one of the means of enzymatic oxidation envisaged here have been described above and relate in particular to monosaccharides, disaccharides and their respective derivatives, for example, those which have already been oxidised.

The term "means of enzymatic oxidation" within the context of the present invention means, in particular, the oxidoreductases of group 1.1.3 within the meaning of the document "ENZYME NOMENCLATURE" mentioned above and mixtures of at least any two of these enzymes, it being specified that said enzymes may be used in the free form or immobilised on a support, such as they are, in the partly or wholly purified form and/or by means of organisms which synthesise said enzymes.

By way of example, the means of enzymatic oxidation may be chosen from enzymes or mixtures of enzymes having at least one of the activities of glucose oxidase, hexose oxidase, galactose oxidase, pyranose oxidase, L-sorbose oxidase, cellobiose oxidase, L-gulonolactone oxidase, L-galactononolactone oxidase, alcohol oxidase, secondary alcohol oxidase or (S)-2-hydroxyacid oxidase, and their respective equivalents, current or future.

Advantageously, the means of enzymatic oxidation has at least one of the glucose oxidase, hexose oxidase, galactose oxidase or pyranose oxidase activities.

It may be, in particular, a preparation based on partly or wholly purified enzyme(s) in the free form or immobilised on a support, having a pyranose oxidase and/or glucose oxidase activity, or based on organism(s), in the free form or immobilised on a support, which synthesise this type of enzyme(s).

Such organisms, enzymatic preparations and enzymes which may advantageously be recycled, are described in the above-mentioned patents and scientific articles which form an integral part of the present description. They may, by way of example, be derived from (consist of) any of the following organisms:

*Polyporus obtusus, Trametes multicolor, Coriolus versicolor, Lenzites betulinus, Oudemansiella mucida, Aspergillus flavus* capable of synthesising, inter alia, pyranose oxidase,

*Aspergillus niger, Aspergillus oryzae* capable of synthesising, inter alia, glucose oxidase, and all their taxonomic and/or functional equivalents, current or future, of natural origin or otherwise, resulting in particular from treatments, mutations or genetic manipulations.

Preferably, the means of enzymatic oxidation has a pyranose oxidase activity.

According to a variant of the process according to the invention, the enzymatic oxidation step is carried out in the presence of a ratio of catalase/oxidoreductase activity(C/O ratio) as specified above, of less than 1000, and particularly
  less than 500, preferably less than 200, if the oxidoreductase consists of pyranose oxidase, or
  less than 40 if the oxidoreductase consists of glucose oxidase.

It should be recalled here that a preparation of oxidoreductase may, despite continuous efforts to purify the enzyme, exhibit simultaneously a relatively high catalase activity which is relatively intimately associated with it physically. This is due in particular to as yet incomplete purification and/or recycling from a medium which also contained catalase. The use of said oxidoreductase may therefore involve, particularly due to its recycling, the concomitant use of an "endogenous" catalase activity which should be distinguished from an "exogenous" catalase activity, i.e. supplied in a predetermined manner, independently of the oxidoreductase activity, simultaneously or otherwise with the latter.

According to a variant of the process according to the invention, the enzymatic oxidation step is carried out in the absence of any exogenous supply of catalase activity.

According to another variant, the means of enzymatic oxidation and the metal (ruthenium and/or palladium) are immobilised on the same support.

The concentration of the organic material used as a substrate of the means of enzymatic oxidation is not subject to any particular constraint as regards the prior art. The organic material may be supplied in particular in the form of a solution having a dry substance ("DS") content in the range 2% to 70%, particularly from 4% to 60%. It may be, for example, a glucose solution having a DS of more than 5%, particularly in the range 6% to 55%, which may be used as a substrate of pyranose oxidase or glucose oxidase. In practice, the enzymatic oxidation reaction is generally carried out at a temperature in the range 15° C. to 60° C., for example, in the range 20° C. to 35° C. if the means of enzymatic oxidation consists of pyranose or glucose oxidase.

The other reaction parameters are those generally found in the literature, including those concerning aeration, agitation and the pH of the reaction medium.

The Applicant company has found, however, that in the case of pyranose oxidase, the pH of the reaction mixture was advantageously above about 5.5 and particularly in the range about 5.6 to 6.5.

As mentioned, the process according to the invention makes it possible, remarkably, to obtain an oxidised material such as glucosone with a very high yield and selectivity from glucose within very short periods of time. If the means of oxidation has pyranose oxidase activity, the process according to the invention may therefore be characterised advantageously by the fact that the enzymatic oxidation step has a duration of less than 6 hours, preferably less than 5 hours.

Consequently, a new, simple, effective, inexpensive and very selective means is now available for obtaining oxidised organic materials.

This means is particularly suitable for the preparation of a saccharide composition containing at least one monosaccharide or a disaccharide, preferably selected from the group comprising glucose, galactose, mannose, xylose, sorbose, maltose, lactose and any mixtures of at least any two of these products, oxidised in at least one place and optionally lactonised, particularly for the preparation of a composition based on at least one product selected from the group comprising glucosone, galactosone, xylosone, glucosyl-glucosone, 2,5-diketo-fructose, gluconic acid, galactonic acid, 2-keto-gluconic acid, 2-keto-glucaric acid, 2,5-diketo-gluconic acid, isoascorbic acid, said acids being in the free and/or lactonised and/or salt form, and any mixtures of at least any two of said products.

Due, in particular, to their purity, the oxidised organic materials obtained in accordance with the invention may undergo advantageously, if desired, one or more subsequent modification steps, particularly of a chemical nature.

The present invention relates in particular to a process as described above, characterised in that it comprises, subsequent to the enzymatic oxidation step in the presence of ruthenium and/or palladium, at least one additional step involving the reduction or oxidation of the enzymatically oxidised, optionally purified organic material.

The reduction step may take place enzymatically as described in the articles by HALTRICH and LEITNER mentioned above. Advantageously, it is a catalytic hydrogenation step as described in the patents WO 81/03666, U.S. Pat. No. 4,321,324 and U.S. Pat. No. 4,423,149 mentioned above.

By way of example, the glucosone preparation obtained from glucose in the presence of pyranose oxidase and ruthenium and/or palladium may, particularly due to its low content of formic acid or of other species acting as catalyst poisons, undergo advantageously an additional oxidation or catalytic hydrogenation step.

Another undeniable economic advantage of the process according to the invention is, moreover, that it allows the recycling of the ruthenium and/or palladium used during the enzymatic oxidation step for the purpose of using it during a subsequent catalytic hydrogenation step.

According to one variant, this process is characterised, therefore, in that it comprises an additional catalytic hydrogenation step, continuous or batchwise, this being preferably also carried out in the presence of ruthenium and/or palladium recycled from the previous enzymatic oxidation step or not recycled.

This process may therefore be used advantageously for the preparation of a saccharide composition containing at least one product selected from the group comprising fructose, sorbitol, mannitol, tagatose, hydrogenated or not hydrogenated, glucosyl-sorbitol, glucosyl-mannitol and any mixtures of at least any two of these products.

According to another variant of the process according to the invention, the enzymatic oxidation step is carried out continuously. Thus, the organic material that has to undergo said step is introduced continuously into the reaction medium and the oxidised organic material that has undergone said step, for example, glucosone, is drawn off, also continuously, from said reaction medium.

In this case, the ruthenium and/or palladium (on a support) may be used advantageously in the form of granules which are placed in a perforated and generally fixed vessel immersed in the reaction medium. The metal granules may thus remain in continuous contact with the reaction medium.

Moreover, the oxidised organic material may, according to another variant, advantageously undergo, likewise continuously or batchwise, at least one subsequent filtration step, for example, microfiltration and/or ultrafiltration, with a view in particular to allowing the continuous or batchwise recycling of all or part of the means of enzymatic oxidation and/or the metal (ruthenium and/or palladium) used beforehand. The oxidised organic material thus purified, for example, glucosone, may then undergo, as already mentioned, a subsequent, particularly continuous, hydrogenation step.

The present invention will be described in more detail with the aid of the examples below which are in no way restrictive.

EXAMPLE 1

One liter of a 10% glucose solution, 1 ml of antifoaming agent (PEG), 5 g of bovine serum albumin (BSA) are introduced into a 2 l reactor together with 2000 units of pyranose oxidase (P2O) supplied in the form of a liquid enzyme preparation derived from Trametes multicolor and having an endogenous catalase activity such that its ratio of catalase/oxidoreductase activity (C/O ratio) is about 50/1.

The activity of catalase is measured according to the UV method described in point 3.9.1. in "Methods of Enzymatic Analysis" by BERGMEYER et al, 3rd edition, 1983, vol. III, "Enzymes 1: Oxidoreductases, Transferases".

The activity of pyranose oxidase is measured according to the article by LEITNER mentioned above.

The onset of the reaction (TO) is defined as corresponding to the moment when glucose and P2O are brought into contact with one another.

The reaction medium is kept under conditions of constant stirring (500 rpm), aeration (1 l of air/l of medium/minute) and temperature (30° C.). The pH of the medium is controlled to a value of 5.8 using 1 M potassium bicarbonate.

During this test (TEST T1), the content of the desired oxidised product in the reaction medium, namely glucosone (hereinafter known as "GLO2") is measured, and also, optionally, the residual glucose content ("GLU") and the content of unwanted oxidised products such as arabinonic acid (in the free and lactonised form—known collectively as "ARA"), formic acid ("FOR") or acetic acid ("ACE").

TESTS T2 to T4 and A to E are carried out under the same general conditions as those used for TEST T1 except that, at TO or around TO, the following are introduced additionally into the reaction medium, respectively:

TEST T2: 2 g of "SX PLUS" activated carbon from NORIT,

TEST T3: $8 \times 10^4$ units of "SIGMA C 30" exogenous catalase,

TEST T4: $3 \times 10^6$ units of "SIGMA C 30" exogenous catalase,

TEST A: 1.16 g of platinum on activated carbon supplying about 0.05% of metal (Pt), expressed as dry weight of metal/total dry weight of the reaction medium.

TEST B: 2 g of Raney nickel supplying about 2% of metal (Ni),

TEST C: 2 g of Raney copper supplying about 2% of metal (Cu),

TEST D: 2 g of ruthenium on activated carbon supplying about 0.05% of metal (Ru), TEST E: 1.37 g of palladium on activated carbon supplying about 0.05% of metal (Pd).

For each of TESTS T1 to T4 and A to E, the results obtained at TX, i.e. X hours after TO, in terms of the glucosone "GLO2" concentration of the reaction medium and, optionally, the concentration of other compounds, are given below, the percentages being expressed in terms of the dry weight of the product sought over the total dry weight of the reaction medium.

| TEST | TX (h) | GLO2 % | GLU % | ARA % | FOR % | ACE % |
|---|---|---|---|---|---|---|
| T1 | 4 | 38.3 | 60.9 | NS | NS | NS |
| T2 | 4 | 86.8 | 12.2 | NS | NS | NS |
| T3 | 6 | 74 | 25 | NS | NS | NS |
| T4 | 4 | 54.5 | 45.1 | abs | 0.08 | NS |
| A | 5 | 48.0 | 48.5 | NS | NS | NS |
| B | 3 | 78.8 | 14.2 | 4.2 | 1.5 | 1.3 |

-continued

| TEST | TX (h) | GLO2 % | GLU % | ARA % | FOR % | ACE % |
|------|--------|--------|-------|-------|-------|-------|
| C    | 3.5    | 22.5   | 75    | NS    | NS    | NS    |
| D    | 4      | 98.7   | abs   | 1.0   | 0.2   | 0.06  |
| E    | 4.5    | 95.0   | abs   | 4.1   | 0.8   | <0.02 |

NS = product not sought during the analysis
Abs = product not detected during the analysis Taken as a whole, these results show that metals such as platinum but also nickel and copper cannot be used effectively in complex and specific media of the kind constituted by the enzymatic oxidation media envisaged here.

Additional analyses also showed:
a) that in the presence of platinum, about 90% of the pyranose oxidase activity was inhibited after 5 hours' reaction and that continuing the reaction gave rise to only a small increase in the glucosone concentration, a significant part ($\approx$10%) of the residual glucose being converted to unwanted co-products;
b) that in the presence of copper, the pyranose oxidase activity was completely inhibited at the end of 3.5 hours' reaction, a further addition of 2000 units of pyranose oxidase itself being rendered completely ineffective in 15 minutes;
c) that in the presence of nickel, more than 40% of the pyranose oxidase activity was inhibited after 3 hours' reaction with, moreover, very significant solubilisation ($\approx$30%) of the metal in the medium.

Conversely, these results show very surprisingly that ruthenium and palladium may be combined advantageously with an oxidoreductase such as pyranose oxidase with a view to obtaining glucosone within very short periods, i.e. of the order of about 4–5 hours, with complete conversion of the glucose and very high selectivity.

In the absence of such metals and with a particularly high catalase (endogenous+exogenous)/oxidoreductase ratio, namely greater than $1.5 \cdot 10^3$ as in the case of TEST T4, it is not possible to obtain, after 4 hours' reaction, a degree of conversion of glucose reaching 60%.

Activated carbon is able to improve this degree of conversion and to reach, in 4 hours, a value of around 87% (86.8%—cf. TEST 2). However, the Applicant company ascertained that if the reaction is allowed to continue in this way, i.e. in the presence of activated carbon but in the absence of ruthenium and/or palladium, the reaction slows down considerably with the generation of large amounts of unwanted co-products. Thus, after 5 hours' reaction, the production of glucosone is still less than 90% (89.8%) with a very significant residual glucose concentration (3.5%) and a relatively high concentration of unwanted co-products (6.3%).

An additional test, identical to test D except that 0.125% of ruthenium are introduced (instead of 0.05%) confirmed the possibility of obtaining, after 4 hours' reaction, a degree of glucose conversion which is at least equal to 90% with a selectivity which is also remarkable.

EXAMPLE 2

This example explored the advantage of using 0.005% of ruthenium in combination with a glucose oxidase preparation (1000 units/l of medium) having an endogenous catalase activity (ratio of catalase/oxidoreductase activity of 7/1) with a view to converting the glucose (solution containing 150 g/l) to gluconic acid.

After 5 hours' reaction at 33° C. and at pH 5.5 (controlled by 50% NaOH), it was observed that in the presence of ruthenium the degree of conversion of glucose to gluconic acid ($\approx$34%) was at least 3 times greater than that obtained in the absence of such a metal ($\approx$10%).

What is claimed is:

1. In a process consisting in converting a saccharide material comprising an enzymatic oxidation step during which the saccharide material undergoes an oxidation under the action of an enzymatic oxidizing agent capable of generating hydrogen peroxide, the improvement consisting in that said enzymatic oxidizing agent is a pyranose oxidase, said oxidation step being carried out in the presence of:

a ratio of catalase/oxidase activity of less than 500 and;
0.001% to 1% of a metal selected from ruthenium, palladium or mixtures thereof, these percentages being expressed as total dry weight of ruthenium and palladium with respect to the total dry weight of the reaction medium;

said enzymatic oxidation step being performed in less than 6 hours.

2. The process according to claim 1, wherein the metal is present in a quantity in the range 0.005% to 0.2%

3. The process according to claim 1, wherein the saccharide material is selected from the group consisting of monosaccharides, disaccharides, oxidised or hydrogenated derivatives of monosaccharides and disaccharides and any mixtures of at least any two of these products.

4. The process according to claim 1, wherein the pyranose oxidase is used in the free form or immobilised on a support, in the partially or completely purified form and/or by means of organisms which synthesize said pyranose oxidase.

5. The process according to claim 1, wherein the enzymatic oxidation step is carried out in the presence of a ratio of catalase/oxidoreductase activity of less than 200.

6. The process according to claim 1, wherein it comprises, subsequent to the enzymatic oxidation step, at least one additional step of reduction or of oxidation of the optionally purified, enzymatically oxidised saccharide material.

7. The process according to claim 6, wherein the additional step consists of a catalytic hydrogenation step, continuous or batchwise.

8. The process according to claim 7, wherein the catalytic hydrogenation step is being carried out in the presence of ruthenium and/or palladium recycled or not from the previous enzymatic oxidation step.

9. The process according to claim 1, wherein the saccharide material is glucose, the enzymatic oxidation step is carried out in the presence of 0.005 to 0.125% ruthenium and wherein a degree of glucose conversion of at least equal to 90% is obtained after 4 hours' reaction.

* * * * *